(12) United States Patent
Han et al.

(10) Patent No.: US 12,227,729 B2
(45) Date of Patent: Feb. 18, 2025

(54) METHODS AND SYSTEMS FOR HIGH-THROUGHPUT CELL PROCESSING

(71) Applicant: CELLFE, INC., Alameda, CA (US)

(72) Inventors: Sewoon Han, Albany, CA (US); Alexander Alexeev, Atlanta, GA (US); Todd Sulchek, Atlanta, GA (US)

(73) Assignee: CellFE, Inc., Alameda, CA (US)

( * ) Notice: Subject to any disclaimer, the term of this patent is extended or adjusted under 35 U.S.C. 154(b) by 620 days.

(21) Appl. No.: 17/561,910

(22) Filed: Dec. 24, 2021

(65) Prior Publication Data

US 2022/0204908 A1     Jun. 30, 2022

Related U.S. Application Data

(60) Provisional application No. 63/130,583, filed on Dec. 24, 2020.

(51) Int. Cl.
   *C12M 3/00*     (2006.01)
   *B01L 3/00*     (2006.01)
   (Continued)

(52) U.S. Cl.
   CPC ............ *C12M 27/10* (2013.01); *C12M 23/06* (2013.01)

(58) Field of Classification Search
   CPC .............................. C12M 27/10; C12M 23/06
   See application file for complete search history.

(56) References Cited

U.S. PATENT DOCUMENTS

| 6,544,423 B1 | 4/2003 | Baurmeister et al. |
| 7,807,451 B2 * | 10/2010 | Kanegasaki ........ B01L 3/50273 436/63 |

(Continued)

FOREIGN PATENT DOCUMENTS

| WO | 2020026047 A1 | 2/2020 |
| WO | 2022109113 A1 | 5/2022 |

OTHER PUBLICATIONS

Barber "A Technic for the Inoculation of Bacteria and Other Substances into Living Cells" The Journal of Infectious Diseases, Apr. 12, 1911, vol. 8, No. 3 (Apr. 12, 1911), pp. 348-360.

(Continued)

*Primary Examiner* — Nathan A Bowers
(74) *Attorney, Agent, or Firm* — Polygon IP, LLP

(57) ABSTRACT

Described herein are methods and systems for cell processing or, more specifically, for introducing various payloads into cells. These methods and systems use a mechanoporation approach in which cells are rapidly compressed and then released to relax while absorbing the payload. More specifically, these methods and systems enable high-throughput mechanoporation with various clogging mitigation features. A cell processing apparatus comprises a shell with an inner shell cylindrical surface, a core with an outer core cylindrical surface, and ridges, supported on and protruding away from one of the inner shell cylindrical surface and the outer core cylindrical surface. The core is disposed inside the shell. The outer core cylindrical surface is concentric with the inner shell cylindrical surface. Each of the ridges forms a ridge gap with the other one of the inner shell cylindrical surface and the outer core cylindrical surface.

20 Claims, 10 Drawing Sheets

(51) Int. Cl.
*C12M 1/12* (2006.01)
*C12M 3/04* (2006.01)

(56) References Cited

U.S. PATENT DOCUMENTS

| | | | |
|---|---|---|---|
| 8,356,714 | B2 | 1/2013 | Sulchek et al. |
| 10,717,084 | B2 | 7/2020 | Sulchek et al. |
| 10,900,886 | B2* | 1/2021 | Lee .................... G01N 15/1433 |
| 11,198,127 | B2 | 12/2021 | Sulchek et al. |
| 11,268,892 | B2 | 3/2022 | Sulchek et al. |
| 2007/0072290 | A1 | 3/2007 | Hvichia |
| 2011/0081674 | A1 | 4/2011 | Han et al. |
| 2014/0227777 | A1 | 8/2014 | Choi et al. |
| 2014/0273229 | A1 | 9/2014 | Meacham et al. |
| 2014/0287509 | A1 | 9/2014 | Sharei et al. |
| 2016/0193605 | A1 | 7/2016 | Sharei et al. |
| 2016/0272961 | A1 | 9/2016 | Lee |
| 2017/0233692 | A1 | 8/2017 | Pawell |
| 2017/0362620 | A1* | 12/2017 | Briechle ................. C12P 19/04 |
| 2018/0003696 | A1 | 1/2018 | Sharei et al. |
| 2018/0016539 | A1 | 1/2018 | Ding et al. |
| 2018/0142198 | A1 | 5/2018 | Sharei et al. |
| 2018/0155669 | A1 | 6/2018 | Pawell |
| 2018/0201889 | A1 | 7/2018 | Sharei et al. |
| 2018/0245089 | A1 | 8/2018 | Sharei et al. |
| 2018/0327706 | A1 | 11/2018 | Qin et al. |
| 2019/0017072 | A1 | 1/2019 | Ditommaso et al. |
| 2019/0111082 | A1 | 4/2019 | Gilbert et al. |
| 2019/0177677 | A1 | 6/2019 | Jonas et al. |
| 2019/0262835 | A1* | 8/2019 | Sulchek .................. C12M 47/04 |
| 2019/0275520 | A1 | 9/2019 | Stewart et al. |
| 2019/0322976 | A1 | 10/2019 | Williams et al. |
| 2019/0382796 | A1 | 12/2019 | Gilbert et al. |
| 2020/0172845 | A1 | 6/2020 | Baker et al. |
| 2020/0316604 | A1 | 10/2020 | Dadgar |
| 2020/0332243 | A1 | 10/2020 | Dadgar et al. |
| 2021/0292700 | A1 | 9/2021 | Han et al. |
| 2021/0379247 | A1* | 12/2021 | Roche ..................... C12M 3/08 |
| 2021/0388390 | A1 | 12/2021 | Bernstein et al. |
| 2022/0105166 | A1 | 4/2022 | Sharei et al. |
| 2022/0213422 | A1 | 7/2022 | Zamarayeva et al. |
| 2022/0298461 | A1 | 9/2022 | Zamarayeva et al. |
| 2024/0240123 | A1* | 7/2024 | Nash ....................... C12M 23/06 |

OTHER PUBLICATIONS

Deng et al. "Intracellular Delivery of Nanomaterials via an Inertial Microfluidic Cell Hydroporator" Nano Lett. 2018, 18, 4, 2705-2710.

Di Carlo, "Enhanced Velocity Gradients within Microfluidics for Cellular Manipulation" In: Baba, Y., Shoji, S., van den Berg, A. (eds) Micro Total Analysis Systems 2002. Springer, Dordrecht. https://doi.org/10.1007/978-94-010-0504-3_66.

DiCarlo et al. "Reagentless mechanical cell lysis by nanoscale barbs in microchannels for sample preparation" Lab on a Chip 3(4):287-91.

Ding et al. "High-throughput Nuclear Delivery and Rapid Expression of DNA via Mechanical and Electrical Cell-Membrane Disruption" Nat Biomed Eng. 2017; 1: 0039.

Hallow et al., "Shear-induced intracellular loading of cells with molecules by controlled microfluidics" Biotechnol Bioeng. Mar. 1, 2008; 99(4): 846-854. doi:10.1002/bit.21651.

Han et al. "CRISPR-Cas9 delivery to hard-to-transfect cells via membrane deformation" Science Advances Aug. 14, 2015.

Jarrell et al. "Intracellular delivery of mRNA to human primary T cells with microfluidic vortex shedding" Sci Rep 9, 3214 (2019).

Kang et al. "Intracellular Nanomaterial Delivery via Spiral Hydroporation" (ACS Nano 2020, 14, 3048-3058).

Liu et al "Cell mechanical and physiological behavior in the regime of rapid mechanical compressions that lead to volume change." Small 16, 1903857-11, 2020.

Liu et al "Microfluidic generation of transient cell vol. exchange for convectively driven intracellular delivery of large macromolecules. Materials Today 21, 703-712, 2018".

Schmiderer et al. "Efficient and nontoxic biomolecule delivery to primary human hematopoietic stem cells using hanostraws" PNAS Sep. 1, 2020 117 (35) 21267-21273.

Sharei et al. "A vector-free microfluidic platform for intracellular delivery" Proc Natl Acad Sci U S A. Feb. 5, 2013; 110(6): 2082-2087.

* cited by examiner

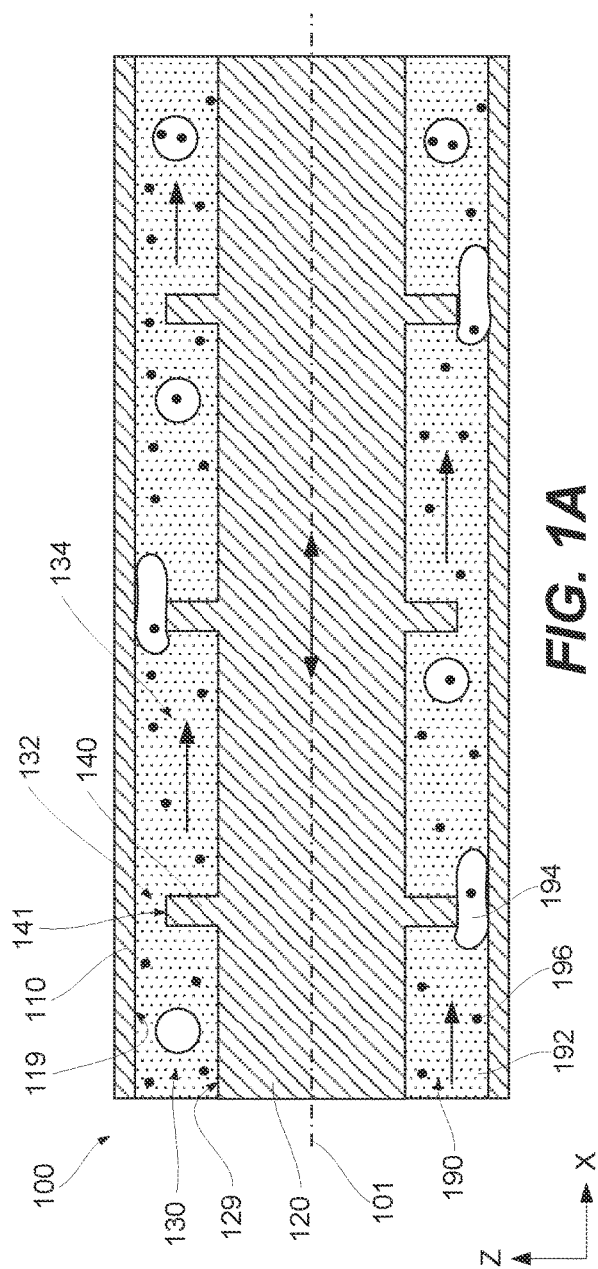
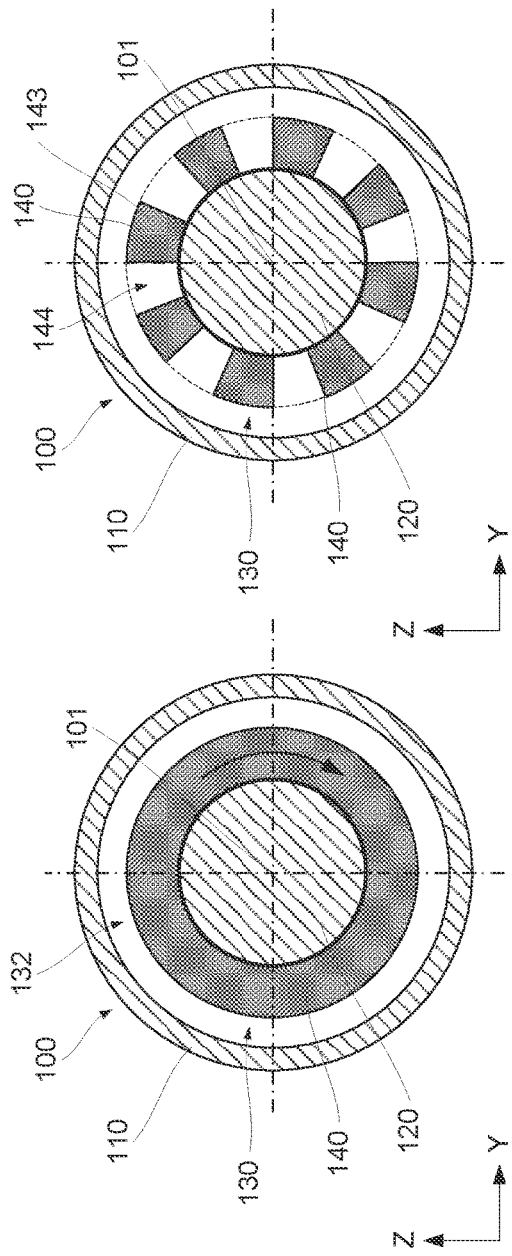

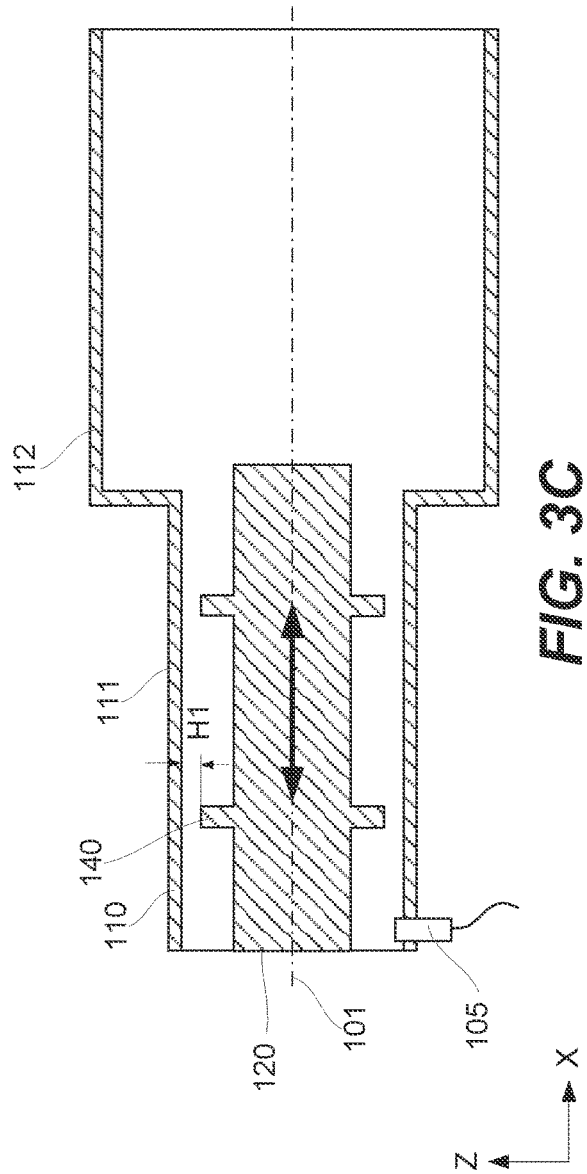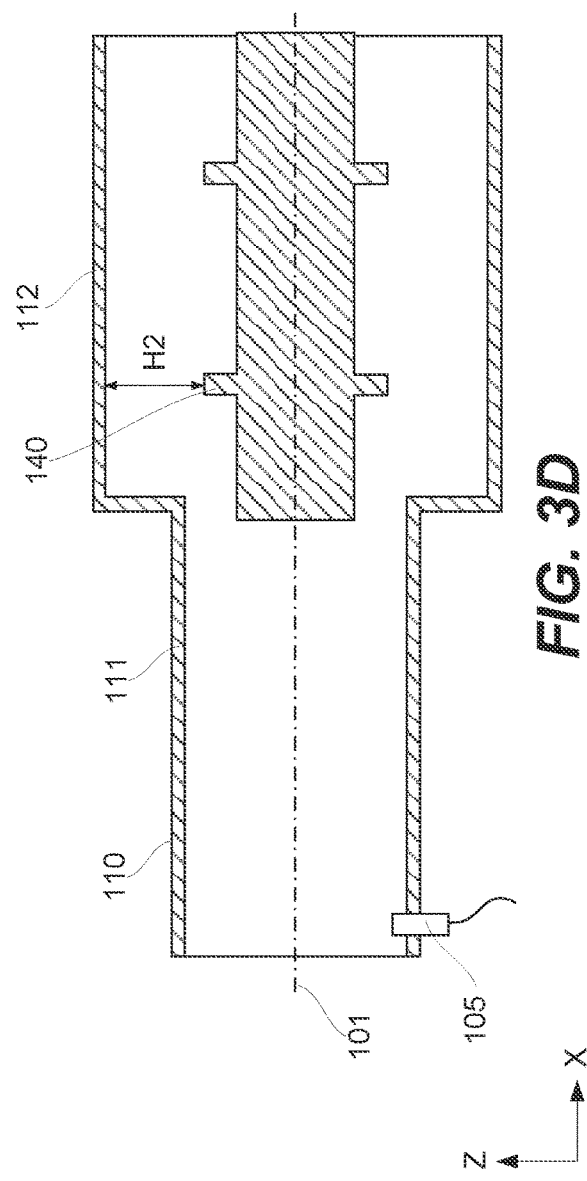

METHODS AND SYSTEMS FOR HIGH-THROUGHPUT CELL PROCESSING

CROSS-REFERENCE TO RELATED APPLICATIONS

This application claims the benefit under 35 U.S.C. § 119(e) of U.S. Provisional Patent Application No. 63/130,583, filed on Dec. 24, 2020, the disclosure of which is incorporated herein by reference in its entirety for all purposes.

BACKGROUND

Intracellular delivery has many valuable applications, such as gene transfection, editing, cell labeling, and cell interrogation. However, conventional delivery methods (e.g., microinjection, electroporation, chemical poration, and sonoporation) have demonstrated low delivery efficiencies and cell viability, especially for large molecules (e.g., molecules with sizes of at least 2000 kDa) and large particles (e.g., particles with sizes of at least 50 nanometers). Furthermore, many conventional delivery methods are not able to process cells at high rates. For example, cells often require individual handling, which significantly slows down processing speeds. What is needed are new methods and systems for high-throughput payload delivery into biological cells.

SUMMARY

Described herein are methods and systems for cell processing or, more specifically, for introducing various payloads into cells. These methods and systems use a mechanoporation approach in which a population of cells is rapidly compressed and then released to relax while absorbing the payload. More specifically, these methods and systems enable high-throughput mechanoporation with various clogging mitigation features. A cell processing apparatus comprises a shell with an inner shell cylindrical surface, a core with an outer core cylindrical surface, and ridges, supported on and protruding away from one of the inner shell cylindrical surface and the outer core cylindrical surface. The core is disposed inside the shell. The outer core cylindrical surface is concentric with the inner shell cylindrical surface. Each of the ridges forms a ridge gap with the other one of the inner shell cylindrical surface and the outer core cylindrical surface.

BRIEF DESCRIPTION OF THE DRAWINGS

FIG. 1A is a schematic cross-sectional side view of a cell processing apparatus, in accordance with some examples.

FIG. 1B is a schematic cross-sectional front view of a cell processing apparatus, in accordance with some examples.

FIG. 1C is a schematic cross-sectional front view of another example of a cell processing apparatus.

FIGS. 3C and 3D are schematic cross-sectional side views of a cell processing apparatus during a cell processing stage (FIG. 3C) and during a cleaning stage (FIG. 3D), in accordance with some examples.

DETAILED DESCRIPTION

Figure 1D:
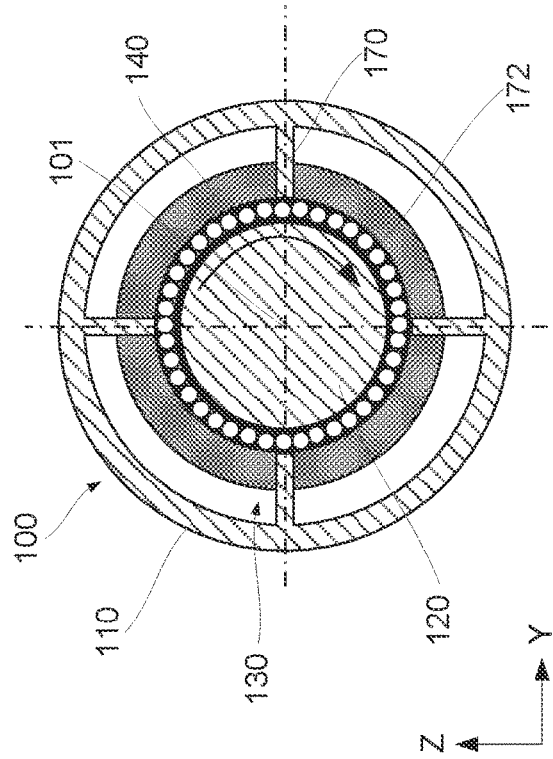
FIG. 1D is a schematic cross-sectional front view of support used to support the core of a cell processing apparatus relative to the shell, in accordance with some examples.

In the following description, numerous specific details are outlined to provide a thorough understanding of the present invention. The present invention may be practiced without some or all of these specific details. In other instances, well-known process operations have not been described in detail to avoid obscuring the present invention. While the invention will be described in conjunction with the specific examples, it will be understood that it is not intended to limit the invention to the examples.

Introduction

As noted above, cell processing methods and systems are based on a mechanoporation approach, in which a population of cells is rapidly compressed and then released to relax and absorb the payload from the surrounding media. Unlike membrane shearing and other conventional methods, the compression used in mechanoporation generally occurs in less than 1 second, often within 10 microseconds to 300 milliseconds. The compression time depends on the flow rate, cell size, ridge geometry, and other factors. Without being restricted to any particular theory, it is believed that such a rapid compression causes the cells to change their volume (i.e., experience volume loss of at least 20% or even at least 30%) rather than simply changing their shapes to adapt to the ridge gaps. The ridge gaps are sometimes referred to as constrictions. The compressed state is a non-natural state for the cells and the cells will attempt to recover to the original volume.

After the compression and volume reduction, the cells are released into a ridge spacing inside a cell processing apparatus. The ridge spacing may be also referred to as a recovery space. In this ridge spacing, the cells are no longer compressed and are allowed to recover. Specifically, the volume of the cells can increase back to normal by absorbing the surrounding media. The media, which surrounds the cells, comprises various payloads (e.g., reagents). These payloads are introduced into the cells as a part of this recovery. For example, plasmids and magnetic nanoparticles have been successfully introduced into stem cells using this technique, mRNA have been introduced into primary peripheral blood mononuclear cells. It should be noted that this technique is suitable for large reagents that are generally cannot be introduced by other microfluidic methods, such as squeezing cells in narrow pores that can lead to mechanical membrane poration followed by diffusion of reagents suspended in the media through the membrane pores. Since the diffusion is slower for larger reagents, such cannot be effective delivery by diffusion into cells. Furthermore, the degree of cell membrane poration proposed by conventional methods is limited to ensure cell viability and avoid cell damage or death. Finally, conventional microfluidic devices for intracellular delivery are prone to clogging because narrow channels are used for achieving high shear and creating membrane pores. However, increasing flow rates to reduce clogging usually results in cell damage and cell death.

The process of compression and recovery may be performed multiple times, e.g., once for each ridge inside the cell processing apparatus. More specifically, each ridge forms a ridge gap with an opposing wall of the apparatus and the cells are compressed while passing through each one of these ridge gaps. In some examples, the ridges may form different gaps. Furthermore, the ridge gaps can be adjusted, e.g., by moving different components of the cell processing apparatus relative to each other. This gap adjustment may be used, e.g., to reconfigure the apparatus (e.g., to process different types of cells), prevent clogging, cleaning, and other like purposes. It should be noted that changing the ridge spacing affects the degree, speed, and/or duration of cell compressions. For example, decreasing the gap formed by sequential ridges allows achieving higher levels of compression.

In general, the methods and systems described herein may be used to deliver a variety of macromolecules to a variety of different cell types. The intracellular delivery is achieved with high throughput and minimal clogging while posing a lower risk of cell death and aggregation than conventional methods.

Examples of Cell Processing Apparatus

FIG. 1A is a schematic cross-sectional side view of cell processing apparatus 100, in accordance with some examples. Cell processing apparatus 100 comprises shell 110, core 120, and ridges 140. Shell 110 comprises inner shell cylindrical surface 119. Core 120 is disposed inside shell 110 and comprises outer core cylindrical surface 129, concentric with inner shell cylindrical surface 119. Inner shell cylindrical surface 119 and outer core cylindrical surface 129 are spaced apart from each other and form interior space 130 of cell processing apparatus 100. In some examples, shell 110 is formed from one or more transparent materials. For example, transparent materials may be used for the integration of optical sensors into cell processing apparatus 100 and process control (e.g., observe clogging within cell processing apparatus 100). On the other hand, nontransparent materials can be used for example to deliver light-sensitive reagents. Materials for shell 110 can include metal, polydimethylsiloxane (PDMS), injection-molded plastics, silicon, glass, and other polymers. Core 120 may be machined from metal (e.g., stainless steel) or plastics. In general, any materials compatible with cell media 190 are within the scope.

Ridges 140 are supported on and protrude away from one of inner shell cylindrical surface 119 and outer core cylindrical surface 129 and toward another one of inner shell cylindrical surface 119 and outer core cylindrical surface 129. Furthermore, each one of ridges 140 forms ridge gap 132 with another one of the inner shell cylindrical surface 119 and outer core cylindrical surface 129. The size of ridge gap 132 is specifically controlled to ensure compression of cells 194 as cells pass through ridge gap 132. More specifically, cell media 190 comprising base media 192, cells 194, and payload 196 is flown through cell processing apparatus 100 or, more specifically, through interior space 130 of cell processing apparatus 100. Cell media 190 flows along center axis 101 of cell processing apparatus 100. A portion of interior space 130 between adjacent ridges 140 is generally larger than the size of cells 194 allow cells 194 to flow unrestricted. However, cells 194 are compressed as they pass through ridge gap 132 or, more specifically, rapidly compressed. For example, depending on the flow rate, the size of each ridge, and other like parameters. Once the compressed cells leave ridge gap 132 and flow into ridge spacing 134, these cells recover and more readily absorb payload 196.

In some examples, cell media 190 is provided into cell processing apparatus 100 using a two-phase droplets generator, such as a through oil flow junction. This generator is used, for example, to encapsulate cells 194 and payload 196, to improve local concentration as further described below.

FIG. 1A and other figures illustrate that ridges 140 are supported on and protrude away from outer core cylindrical surface 129. However, one having ordinary skill in the art would understand examples in which ridges 140 are supported on and protrude away from inner shell cylindrical surface 119. Furthermore, ridges 140 may include two sets, such that one set is supported on and protrude away from inner shell cylindrical surface 119 while the other set is supported on and protrude away from outer core cylindrical surface 129. Each ridge set of these different sets may be offset axially, e.g., along center axis 101 of cell processing apparatus 100. Alternatives, ridges of different sets may overlap.

In some examples, ridges 140 are monolithic with shell 110 or core 120 (e.g., formed from the same material piece). For example, FIG. 1A illustrates ridges 140 being monolithic with core 120. This approach simplified the manufacturing of cell processing apparatus 100. For example, a combination of ridges 140 and core 120 may be fabricated using a lathe. Alternatively, ridges 140 are separate components that are attached to shell 110 or core 120. This approach allows replacing ridges 140, e.g., with a different configuration. It should be noted that cell processing apparatus 100 may be reconfigured by replacing shell 110, core 120, or both. For example, the combination of ridges 140 and core 120, which is shown in FIG. 1A, may be replaced with another combination providing different ridge gaps 132, ridge spacing 134, and/or other like parameters.

FIG. 1A illustrates the cross-sectional profile (in X-Z plane) of ridge 140 being rectangular. However, other shapes of the profile are also within the scope, e.g., cylindrical, trapezoidal, or triangular. In some embodiments, the plurality of compressive surfaces may be orthogonal. Another characterization, at least of rectangular ridges 140, is the length of the ridge surface (forming ridge gap 132) in the X direction, which may be also referred to as ridge thickness. In some examples, the ridge surface length is between about 5 micrometers and 100 microns or, more specifically, between about 20 micrometers and 50 micrometers. Different ridges 140 of the same cell processing apparatus 100 may have different ridge surface lengths. This ridge surface length or the ridge thickness, together with the channel flow rate, defines the period during which a cell is compressed by the ridge. When the ridge thickness is smaller than the average cell size, cell compressions can be compromised as the cell partially can remain in the uncompressed state when passing compression space. When the ridge thickness is much larger than cell size, such as larger than 10 cell diameters, cells can accumulate in the compressive space which can lead to channel clogging.

In some examples, ridge surface 141, which defines ridge gap 132 together with another surface (e.g., inner shell cylindrical surface 119 in FIG. 1A) is parallel to this other surface. In other words, ridge gap 132 is defined by two parallel surfaces. Parallel compressive surfaces allow for a uniform compression for the entire cell. Additionally, the compression surfaces can be converging and/or diverging. Converging surfaces allow increasing cell compression as cells pass the compressive space, increasing the reduction of cell volume. Diverging surfaces can be used to allow cell expansion that accelerates cell motion and prevents clogging.

In some examples, ridge gap 132 is selected based on cell size, compression needed, and other characteristics of intracellular delivery. In some examples, the gap size is between 1 micrometer and 20 micrometers or, more specifically, between 3 micrometers and 8 micrometers. Furthermore, the gap size may be also defined relative to the cell size, which is defined as the average largest cross-sectional dimension of cells 194. More specifically, the ratio of the gap size to the cell defines the compression level of cells 194 as they pass through ridge gaps 132. In some embodiments, this ratio is between 25% and 75% of cell size or between 75% and 100% of cell size, or more specifically, between 30% and 60%. Furthermore, in some examples, the cell size is between 4 micrometers and 20 micrometers or, more specifically, between 6 micrometers and 15 micrometers.

In some examples, the gap size is larger than the cell size, in which case compression of the cells is induced by the fluid layer formed between the cells and the opposing channel surface. Hydrodynamic compression may be used to increase cell viability and to prevent cell damage. In some examples, the ratio between the gap size and the cell size is between 100% and 150% of cell size or between 150% and 500% of cell size or larger.

In some examples, core 120 is movable relative to shell 110 during the operation of cell processing apparatus 100. This movement may be used to switch between the processing position and the cleaning position as further described below with reference to FIGS. 3A-3E. In some examples, this movement may be used to apply additional shear forces to cells 194 as cells 194 pass through ridge gaps 132 and, as such, increase the rate with which payload 196 is absorbed by cells 194. For example, core 120 is rotatable within and relative to shell 110 during the operation of cell processing apparatus 100 as, for example, is schematically shown by an arrow in FIG. 1B. In some examples, core 120 rotates within shell 110 in one direction. Alternatively, the rotation direction changes, e.g., periodically. In the same or other examples, core 120 is linearly translatable along center axis 101 of cell processing apparatus 100 relative to shell 110 during the operation of cell processing apparatus 100 as, for example, is schematically shown by an arrow in FIG. 1A.

In some examples, each or at least one of ridges 140 form a continuous ring around core 120 as, for example, is schematically shown by an arrow in FIG. 1B. In these examples, cells 194 (and the rest of cell media 190) have to pass through each ridge gap 132 as they flow through cell processing apparatus 100. This feature ensures that all cells 194, collected at the outlet of cell processing apparatus 100, have been compressed.

In other examples, each or at least one of ridges 140 comprises petals 143 separated from each other by petal gaps 144 as, for example, is schematically shown by an arrow in FIG. 1C. Petal gaps 144 allow for uncompressible cells (e.g., particularly large cells or damaged cells) to pass through cell processing apparatus 100 without causing clogging. In some examples, this petal feature is coupled with the core-rotation feature such that the angular positions of petal gaps 144 change over time. In more specific examples, petals 143 and petal gaps 144 of two adjacent ridges 140 are angularly offset. This feature created a torturous path through cell processing apparatus 100 thereby ensuring that cells 194 encounter at least one ridge gap 132 on their way.

Petals 143 can take various shapes, e.g., having a cylindrical shape, a rectangular shape, a rhomboid shape, an ellipsoid shape, and a triangular shape. In some examples, petals 143 are spaced evenly around the circumference of core 120, e.g., as schematically shown in FIG. 1C. Petal gaps 144 can be smaller than the cell size such that the cells are compressed by petals 143 as the cell flow-through cell processing apparatus 100. It should be noted that the cells can pass through petal gaps 144, the gap between petals 143 and shell 110, or through both types of gaps. In some examples, the size of petal gaps 144 is similar (e.g., within 25% or even within 10%) to the gap between petals 143 and shell 110. Alternatively, the size of petal gaps 144 is different from to the gap between petals 143 and shell 110. In some examples, the size of petal gaps 144 is between 30% and 95% of the cell size or, more specifically, between 50% and 70% of the cell size. In some examples, the size of petal gaps 144 is about the cell diameter or even greater than the cell size such that cell deformation is accomplished by hydrodynamic interactions with the fluid flow through petal gaps 144. For example, hydrodynamic compression can be used to improve cell viability in comparison to, e.g., mechanical compression. Specifically, the fluid flowing through petal gaps 144 induces cell deformation. As such, the size of petal gaps 144 can be between 80% and 150% of the cell diameter, or between 150% and 500% of cell the diameter. The gap between petals 143 and shell 110 is preferably less than cell size. Specifically, this gap may be between 1% and 10% of the cell size or between 10% and 50% of the cell size, or between 50% and 100% of the cell size. In some examples, the gap between petals 143 and shell 110 is larger than the cell size such as between 100% and 200% of the cell size or larger. The overall volumetric flowrate, the cross-sectional size of petals 143 (in the direction perpendicular to the flow direction), the size of petal gaps 144, and the size of the gap between petals 143 and shell 110 define the linear flow velocity through petal gaps 144 and the gap between petals 143 and shell 110.

Referring to FIG. 1D, in some examples, cell processing apparatus 100 comprising support structure 170 for supporting core 120 within shell 110 to maintain interior space 130 and, more specifically, to maintain core 120 and shell 110 concentric to each other. For example, FIG. 1D illustrates support structure 170 comprising four components, extending within interior space 130 between shell 110 and core 120. These components may be parts or integrated into either shell 110 or core 120. In some examples, support structure 170 allows for shell 110 to move relative to core 120 axially (e.g., along center axis 101), rotationally (e.g., about center axis 101), or both. For example, support structure 170 may comprise bearing 172.

Figure 1E:
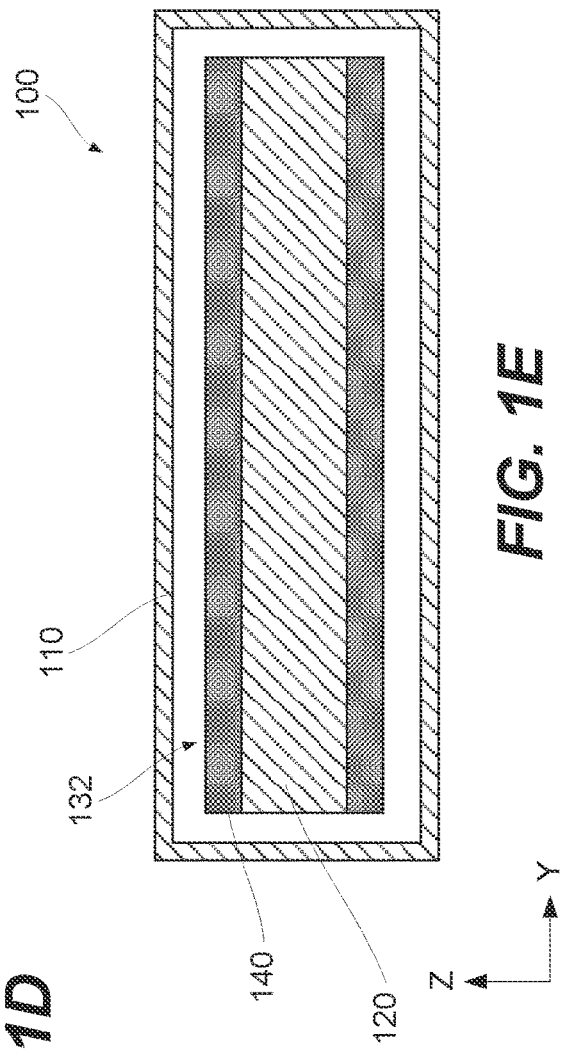
FIG. 1E is a schematic cross-sectional front view of another example of a non-circular cell processing apparatus.

Referring to FIG. 1E, in some examples, cell processing apparatus 100 comprises core 120 and shell 110 that are not circular. For example, FIG. 1E illustrates core 120 and shell 110 having rectangular cross-sections. However, other cross-sectional shapes are within the scope, e.g., square, triangular, oval, polygon, and the like.

Figure 2A:
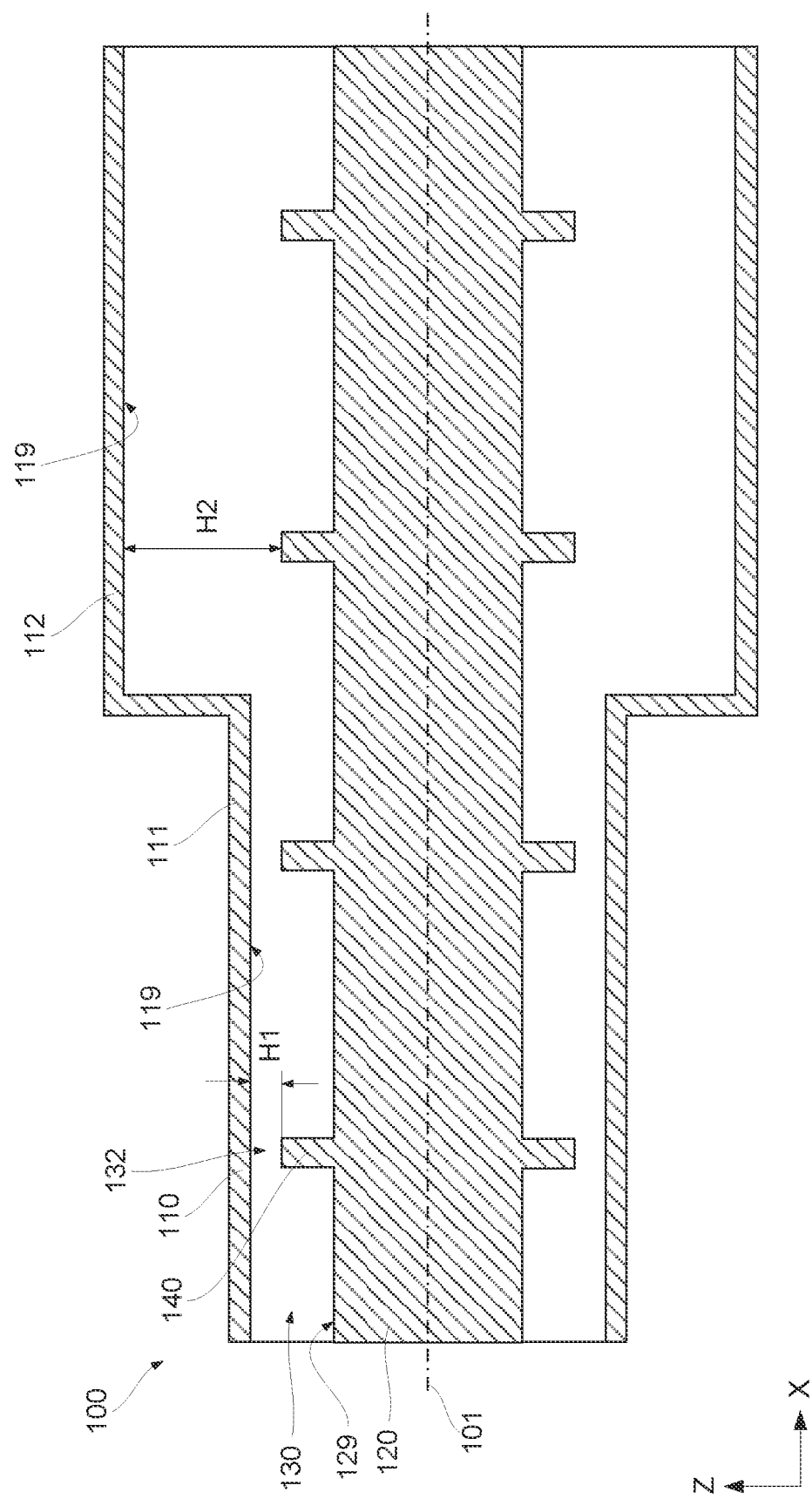
FIG. 2A is a schematic cross-sectional side view of a cell processing apparatus with two shell portions having different inside diameters, in accordance with some examples.

As shown in FIG. 1A and FIG. 2A, in some examples, ridges 140 are supported on and protruding away from outer core cylindrical surface 129. More specifically, the outer radius of ridges 140 is the same for each ridge. In other words, compressive surfaces, formed by the ridges 140, are positioned at the same distance from center axis 101 of cell processing apparatus 100. These compressive surfaces define ridge gaps 132.

Referring to FIG. 2A, in some examples, shell 110 comprises first shell portion 111 and second shell portion 112 such that inner shell cylindrical surface 119 of first shell portion 111 is positioned closer to center axis 101 of cell processing apparatus 100 than inner shell cylindrical surface 119 of second shell portion 112. Since the compressive surfaces, formed by the ridges 140, are positioned at the same distance from center axis 101, ridge gaps 132 are different in first shell portion 111 and in second shell portion 112. More specifically, the size of ridge gaps 132 is less in first shell portion 111 than in second shell portion 112 (H1<H2). As such, the level of compression experienced by cells 194 within first shell portion 111 would be greater than within second shell portion 112. In some examples, first shell portion 111 is positioned before second shell portion 112 along the flow path. In other examples, first shell portion 111 is positioned after second shell portion 112 along the flow path. Furthermore, in some examples, first shell portion 111 and second shell portion 112 overlap.

Figure 2B:
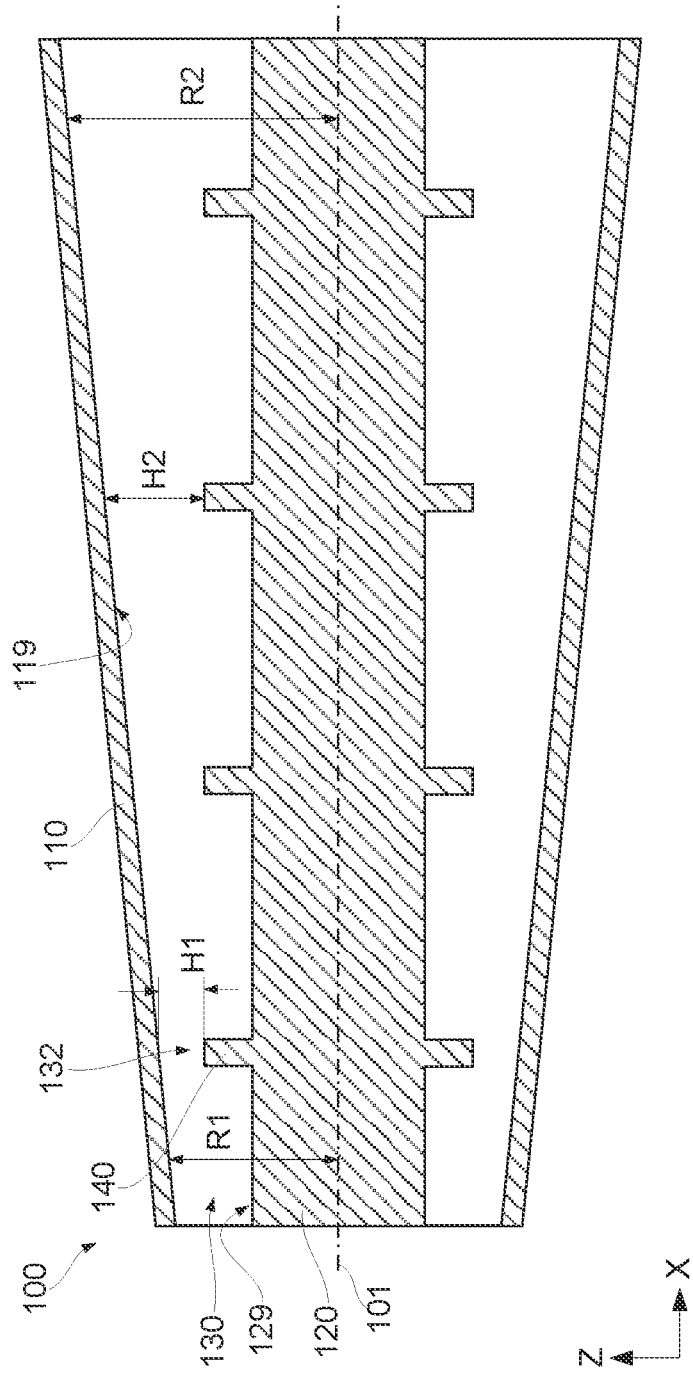
FIG. 2B is a schematic cross-sectional side view of a cell processing apparatus with a tapered shell, in accordance with some examples.

Referring to FIG. 2B, in some examples, the radius of inner shell cylindrical surface 119 of shell 110 gradually increases along a center axis 101 of cell processing apparatus 100. In these examples, the compression of cells 194 also changes as these cells 194 pass through cell processing apparatus 100. In some examples, the radius of inner shell cylindrical surface 119 and the outer radius of ridges 140 gradually increase along center axis 101. This configuration can be used to alter the velocity of cells as they move along cell processing apparatus 100. Additionally, in some examples, the axial position of shell 110 with respect to core 120 may be changed to increase or decrease the gap size depending on the direction of the shell displacement. When the shell is displaced in the direction of increasing inner radius, the gap size decreases. When the shell is displaced in the direction of decreasing radius, the gap size increases. The ability to adjust the gap size may be used to improve cell processing for cell populations with different biophysical properties.

Figure 2C:
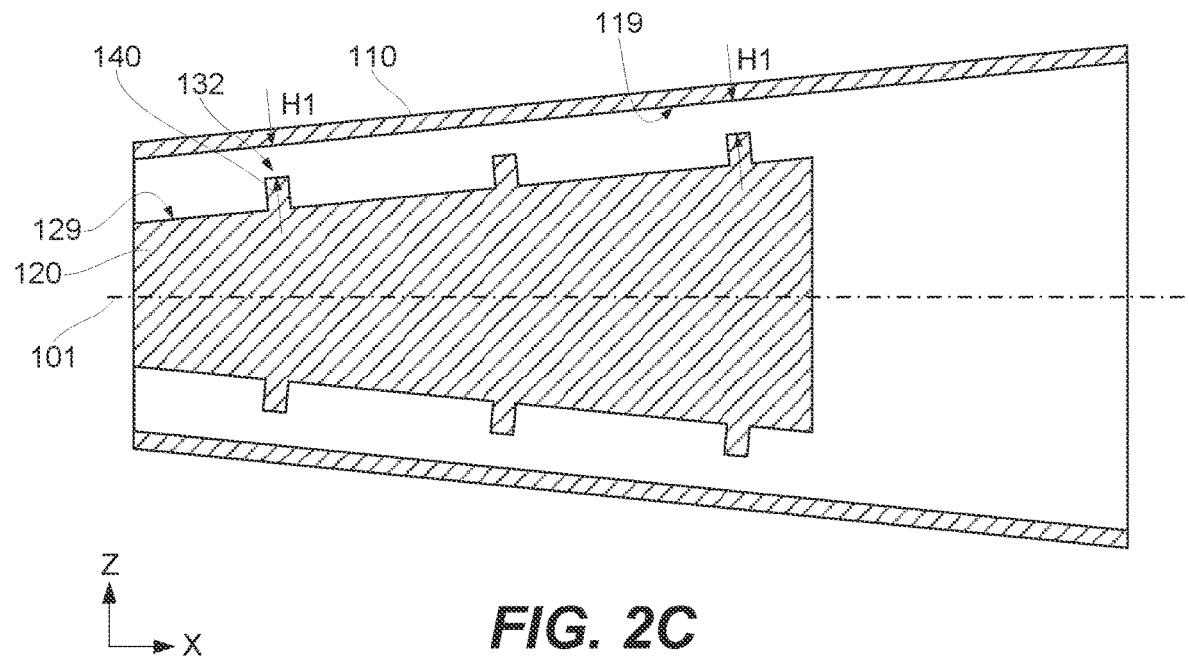
FIGS. 2C and 2D are schematic cross-sectional side views of a cell processing apparatus with a tapered shell and a tapered core at two different positions, in accordance with some examples.
Figure 2D:
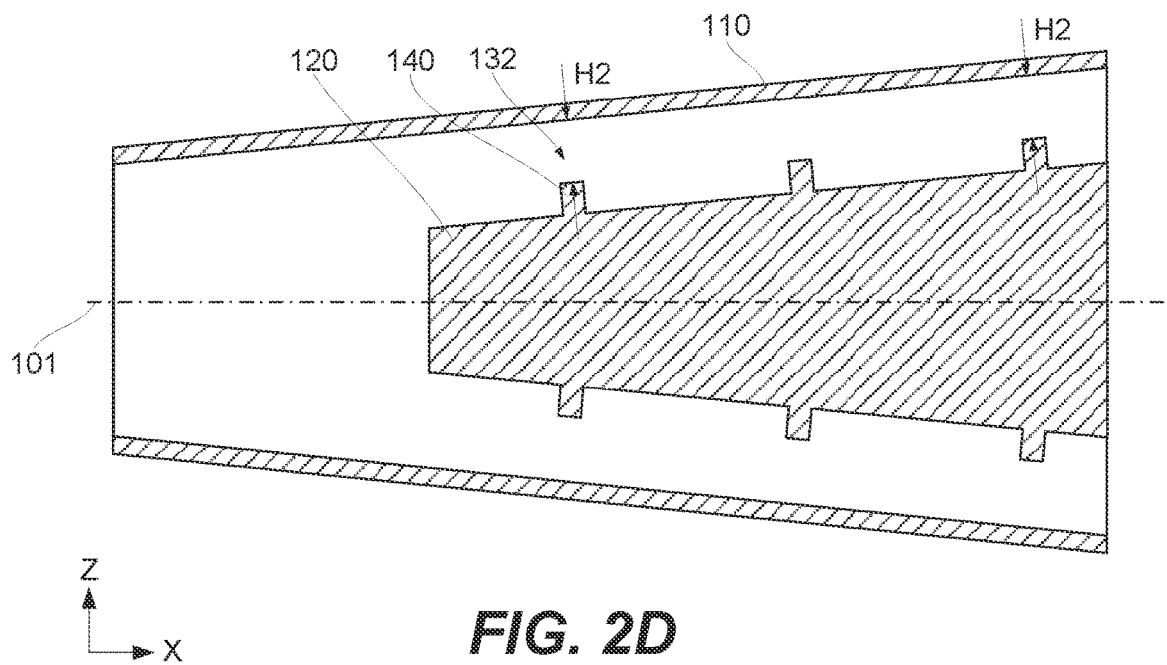

FIGS. 2C and 2D are schematic cross-sectional side views of cell processing apparatus 100 with tapered shell 110 and tapered core 120 at two different positions, in accordance with some examples. In these examples, the taper of shell 110 and core 120 is the same or, more specifically, the angle of inner shell cylindrical surface 119 relative to center axis 101 is the same as the angle of outer core cylindrical surface 129 relative to center axis 101 (of that inner shell cylindrical surface 119 is parallel to outer core cylindrical surface 129). When ridges 140 protrude the same distance from outer core cylindrical surface 129, ridge gap 132 is the same for all ridges (e.g., H1 in FIG. 2C). However, when shell 110 and core 120 are moved relative to each other (e.g., as shown in FIG. 2D), ridge gap 132 changes (e.g., increases to H2 in FIG. 2D). This gap size change depends on the linear movement of shell 110 and core 120 are moved relative to each other and on the angle of inner shell cylindrical surface 119 relative to center axis 101. It should be noted that ridge gap 132 is still the same for all ridges (e.g., H2 in FIG. 2D). This feature can be used to reconfigure cell processing apparatus 100 from one size of ridge gap 132 to another size.

Figure 3A:
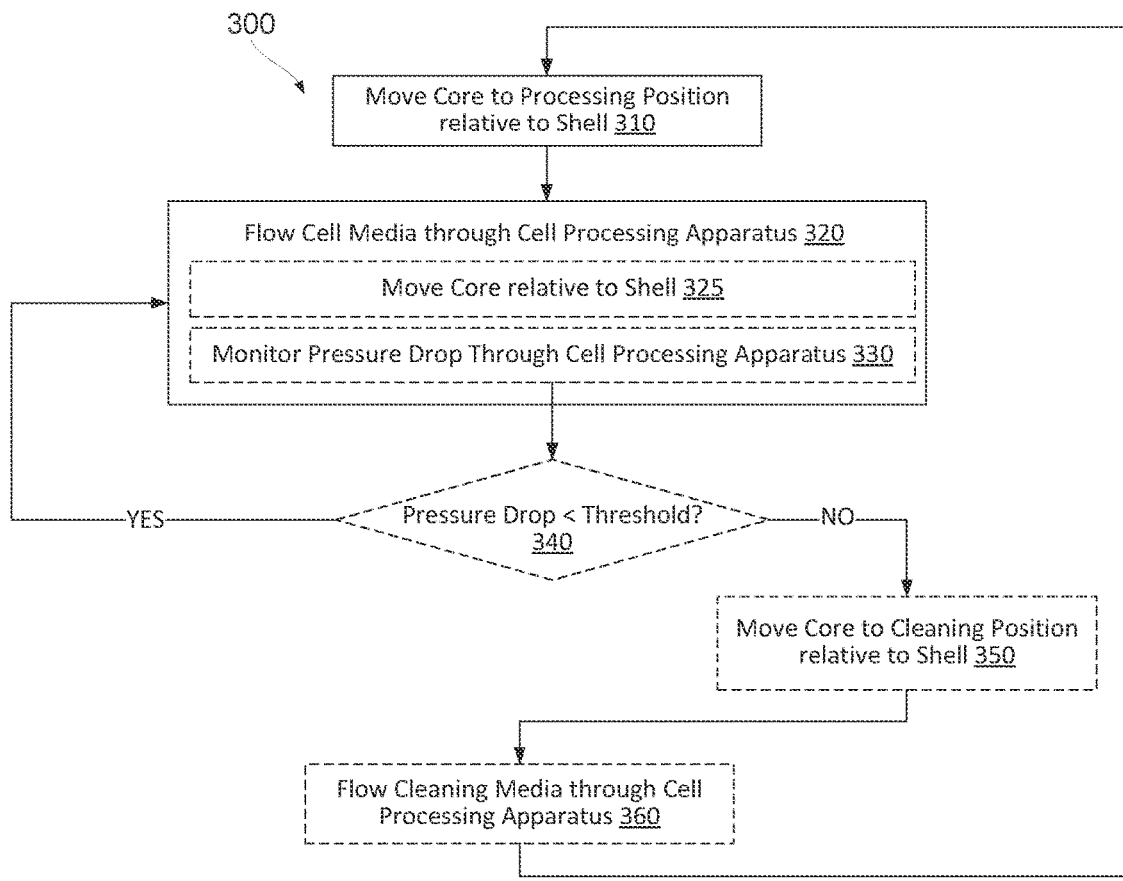
FIG. 3A is a process flowchart corresponding to a method of processing cells, in accordance with some examples.
Figure 3B:
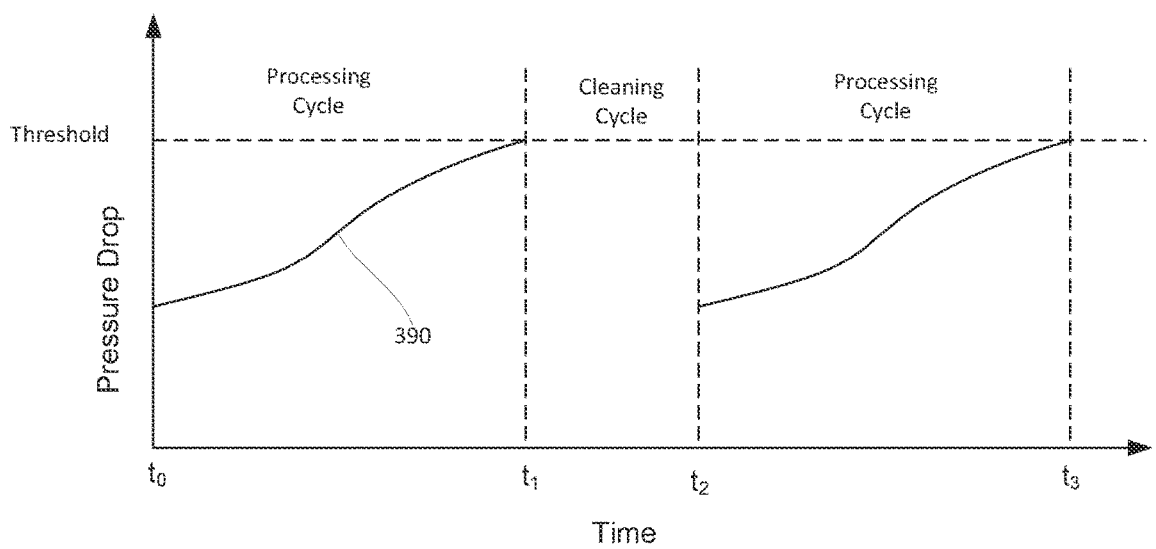
FIG. 3B is a plot of a pressure drop across a cell processing apparatus as a function of time, in accordance with some examples.
Figure 3E:
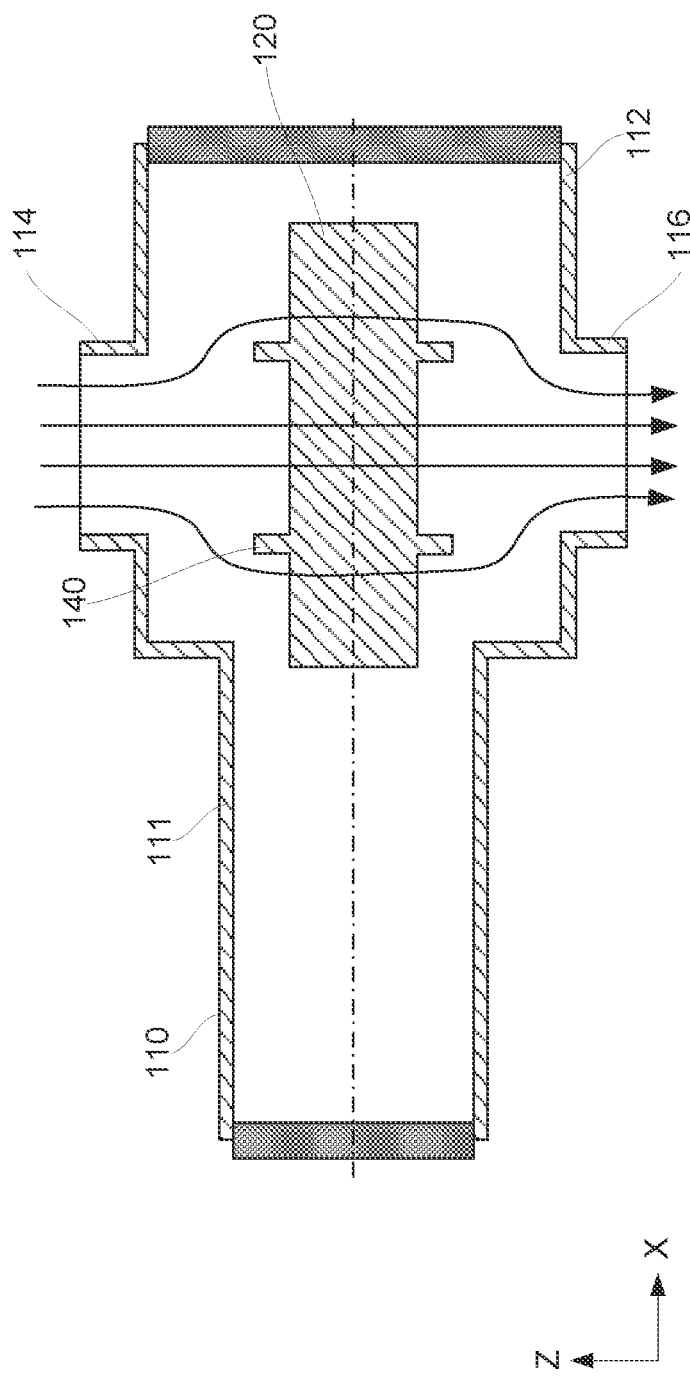
FIG. 3E is a schematic cross-sectional side view of a cell processing apparatus with a cleaning inlet and a cleaning outlet, in accordance with some examples.

Referring to FIG. 3E, in some examples, second shell portion 112 comprises cleaning inlet 114 and cleaning outlet 116. These examples will be further described below with reference to FIGS. 3A-3E.

Examples of Cell Processing Methods

FIG. 3A is a process flowchart corresponding to method 300 of processing cells 194, in accordance with some examples. Method 300 is performed using cell processing apparatus 100 comprising shell 110, core 120 disposed inside shell 110, and ridges 140 extending between shell 110 and core 120 and supported by one of shell 110 or core 120. Various examples of cell processing apparatus 100 are described above.

In some examples, method 300 comprises moving core 120 into a processing position relative to shell 110 (block 310 in FIG. 3A). As noted above, shell 110 comprises inner shell cylindrical surface 119. Core 120 comprises outer core cylindrical surface 129, concentric with inner shell cylindrical surface 119 and forming interior space 130 with inner shell cylindrical surface 119. Each of ridges 140 forms ridge gap 132 with one of inner shell cylindrical surface 119 and outer core cylindrical surface 129 in this processing position. This ridge gap may be referred to as a processing ridge gap.

In some examples, method 300 proceeds with flowing cell media 190 through interior space 130 (block 320 in FIG. 3A). Cell media 190 comprises base media 192, cells 194, and payload 196. During this operation, at least some of cells 194 are compressed as cell media 190 flows through ridge gap 132. This compression causes insertion (e.g., absorption) of payload 196 into cells 194.

In some examples, flowing cell media 190 through interior space 130 comprises moving core 120 relative to shell 110 (block 325 in FIG. 3A). This movement may be used, e.g., to increase the shear stress applied to cells 194 by ridges 140, e.g., as cells 194 pass through ridge gap 132. Furthermore, this movement may be used to reduce clogging within cell processing apparatus 100, e.g., by moving uncompressible cells to petal gaps 144. For example, moving core 120 relative to shell 110 comprises rotating core 120 relative to shell 110. In some examples, moving core 120 relative to shell 110 comprises linearly translating core 120 relative to shell 110 along a center axis 101 of cell processing apparatus 100.

In some examples, flowing cell media 190 through interior space 130 comprises monitoring a pressure drop of cell media 190 through cell processing apparatus 100 (block 330 in FIG. 3A). For example, pressure sensors (e.g., sensor 105 shown in FIGS. 3C and 3D), flow meters, pump power, and/or other indicators may be used for this purpose. The pressure drop indicates the level of clogging of cell processing apparatus 100. For example, FIG. 3B illustrates an example of the pressure drop profile 390 over time. The pressure drop increases as more uncompressible cells get stuck on ridges 140.

In some examples, when the pressure drop through cell processing apparatus 100 exceeds a threshold (decision block 340 in FIG. 3A), method 300 proceeds with moving core 120 from the processing position to the cleaning position relative to shell 110 (block 350 in FIG. 3A). This movement is schematically shown in FIG. 3C (the processing position) and FIG. 3D (the cleaning position). Ridge gap 132 in the cleaning position is greater than in the processing position (H2>H1). This increase in ridge gap 132 allows uncompressible cells to flow past ridges 140 without being compressed. In some examples, moving core 120 from the processing position to the cleaning position comprises linearly translating core 120 relative to shell 110 along center axis 101 of cell processing apparatus 100. As shown in FIGS. 3C and 3D, in the processing position, ridges 140 are surrounded by inner shell cylindrical surface 119 of first shell portion 111. In the cleaning position, ridges 140 are surrounded by inner shell cylindrical surface 119 of second shell portion 112.

In some examples, method 300 proceed with flowing a cleaning media through cell processing apparatus 100 (block 360 in FIG. 3A). During this operation, cell processing apparatus 100 or, more specifically, core 120 is in the cleaning position. Referring to FIG. 3E, in some examples, cell processing apparatus 100 or, more specifically, second shell portion 112 comprises cleaning inlet 114 and cleaning outlet 116. The cleaning media is flown through cleaning inlet 114 and received from cleaning outlet 116. Other portions of cell processing apparatus 100 may be fluidically isolated from second shell portion 112 where the cleaning is performed. As the cleaning media flows around core 120, the cleaning media removes uncompressible cells and other materials stuck on ridges 140.

System Examples

Figure 4:
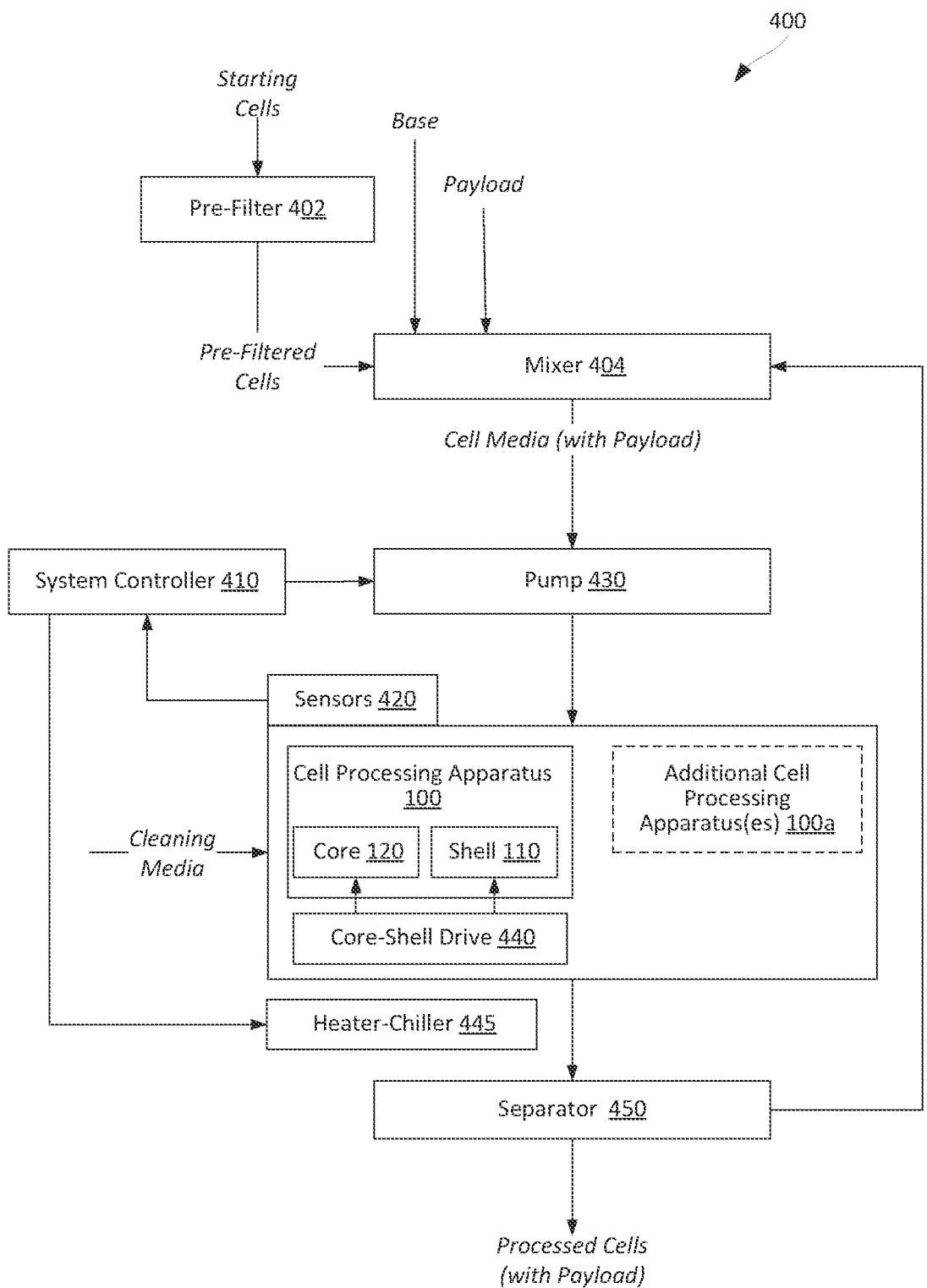
FIG. 4 is a schematic block diagram of a system comprising a cell processing apparatus, in accordance with some examples.

FIG. 4 is a schematic block diagram of system 400 comprising cell processing apparatus 100, in accordance with some examples.

In some examples, system 400 further comprises system controller 410, one or more sensors 420 (e.g., sensor 105 shown in FIGS. 3C and 3D), and pump 430. Another optional component is heater-chiller 445, thermally coupled to or integrated into cell processing apparatus 100. Heater-chiller 445 is used to maintain a target temperature to improve cell viability and to increase delivery efficiency. Furthermore, flow regulators, flow sensors, and/or valves may be used for controlling flow conditions. In some examples, actuators are used to redirect processed and/or unprocessed cells, change flow parameters in the channel, and induce fluid mixing in the channel to improve delivery.

Sensors 420 may be configured to measure one or more characteristics of cells 194 or, more generally, one or more characteristics of media 190 during and after processing. In some examples, sensors 420 are integrated into cell processing apparatus 100 to measure characteristics within the interior of cell processing apparatus 100. Some examples of sensors 420 include, but are not limited to, a thermocouple, a cell counter (e.g., Coulter counter, optical counter), a pressure sensor, and a flow meter. The information about the number of cells that are processed can be used to control the quality of the delivery process and to adjust the process parameters. For example, a fast reduction in cell count at the outlet compared to the inlet can indicate device malfunction such as clogging and leakage. In combination with reduced pressure, reduced cell count can indicate device leakage, whereas when pressure remains constant or elevated, it can indicate clogging. In the latter case, the cleaning procedure can be started by for example temporal increase of channel flow rate. Furthermore, deviation in these and other controlled parameters can be used to interrupt the delivery procedure to prevent the reduction in the product quality due to the introduction of unprocessed and/or under-processed cells. In some examples, pressure and/or flow sensors are used to control flow conditions in the channel.

Pump 430 is configured to deliver media 190 to cell processing apparatus 100 and is fluidically coupled to the inlet of cell processing apparatus 100. Pump 430 may control the flow rate, pressure, and other characteristics.

System controller 410 is configured to receive various inputs and/or to control various operations of different components of system 400. For example, system controller 410 may receive various sensor data. System controller 410 may instruct pump 430 to increase or decrease the flow rate. In some examples, system controller 410 instructs core-shell drive 440 (e.g., a linear actuator, a rotational drive) to move core 120 relative to shell 110. For example, core-shell drive 440 may axially move core 120 relative to shell 110 as described above with reference to FIGS. 1A, 3C, and 3D and/or to rotate core 120 relative to shell 110 as described above with reference to FIG. 1B.

In some examples, system 400 comprises multiple cell processing apparatuses connected in series and/or parallel to each other (e.g., additional cell processing apparatus 100a in FIG. 4). The parallel connection may be used to increase cell throughput. For example, the diameter of each cell processing apparatus 100 may be limited by various manufacturing factors. Furthermore, larger cell processing apparatuses may be prone to clogging by abnormal cells and cell clusters. Instead, using multiple parallel cell processing apparatuses, e.g., with a common inlet and outlet, allows increasing without encountering the issues listed above. Inlet and outlet manifolds may be designed to provide equal distribution of flow to all cell processing apparatuses. To ensure that blockage of one cell processing apparatus will not lead to increased flow rates through other cell processing apparatuses, various sensors, e.g., cell counters and pressure transducers, may be integrated into each cell processing apparatus.

Furthermore, system 400 may comprise pre-filter 402 (e.g., to remove various abnormal cells, mixer 404 (e.g., to combine cells 194 with base media 192 and payload 196 to form cell media 190), and/or separator 450 (e.g., to remove base media 192 and any remaining payload 196, which can be returned into mixer 404).

Additional Examples

Figure 5A:
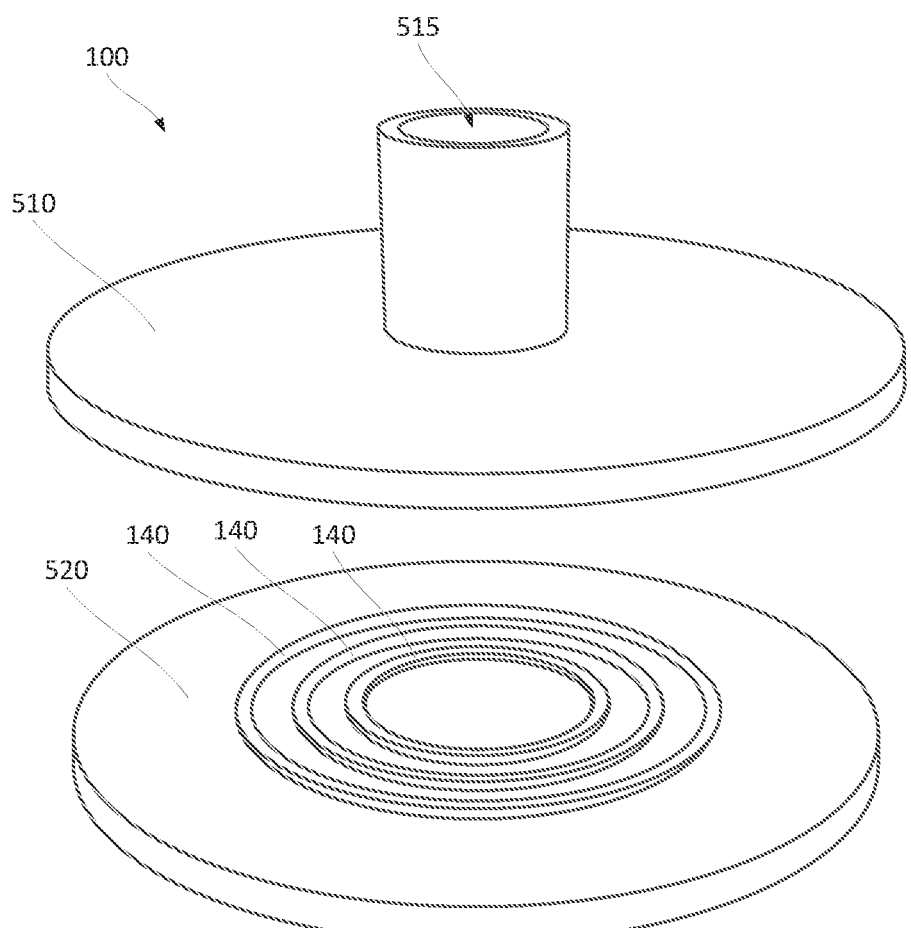
FIGS. 5A and 5B are schematic exploded and cross-sectional views of a cell processing apparatus, in accordance with some examples.
Figure 5B:
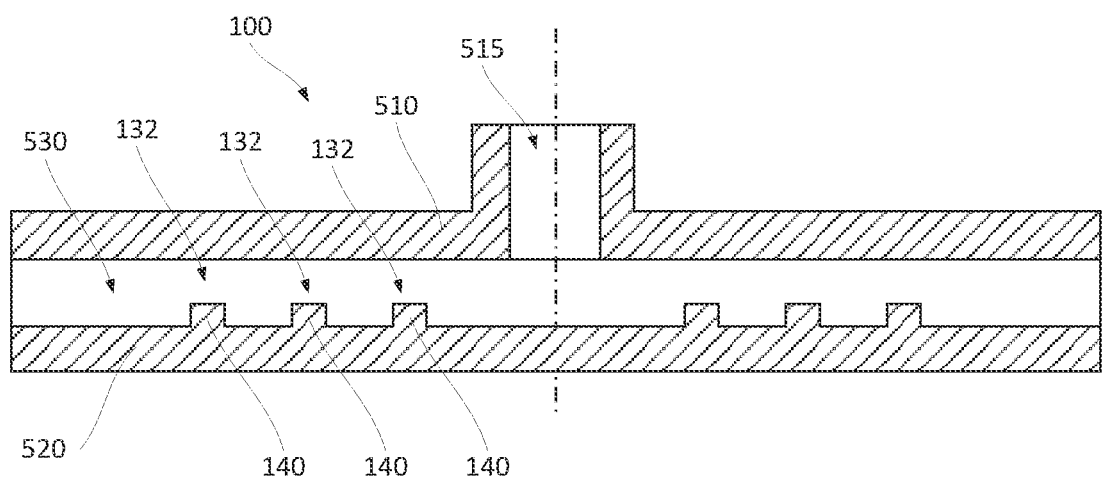

FIGS. 5A and 5B are schematic exploded and cross-sectional views of cell processing apparatus 100, in accordance with some examples. In these examples, cell processing apparatus 100 comprises first component 510 and second component 520, stacked together and forming gap 530. One or both of first component 510 and second component 520 comprise ridges 140, extending into gap 530 and forming ridge gaps 132 as, e.g., is schematically shown in FIG. 5B. Ridges 140 can form rings (e.g., concentric rings) surrounding inlet 515, protruding through first component 510 and/or second component 520. When cell media is supplied through inlet 515, the media flows through ridge gaps 132 subjecting cells to compression and mechanoporation, as described above. For cleaning, first component 510 can be removed from second component 520, i.e., effectively disassembling cell processing apparatus 100.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present examples are to be considered as illustrative and not restrictive.

What is claimed is:

1. A method of processing cells in a cell processing apparatus comprising a shell, a core disposed inside the shell, and ridges extending between the shell and the core and supported by one of the shell or the core, the method comprising:
   moving the core into a processing position relative to the shell, wherein:
      the shell comprises an inner shell cylindrical surface,
      the core comprises an outer core cylindrical surface, concentric with the inner shell cylindrical surface and forming an interior space with the inner shell cylindrical surface, and
      each of the ridges forms a ridge gap with one of the inner shell cylindrical surface and the outer core cylindrical surface in the processing position;
   flowing a cell media through the interior space while monitoring a pressure drop or a flow rate of the cell media through the cell processing apparatus, wherein:
      the cell media comprises a base media, a population of cells, and a payload,
      the cells are compressed as the cell media flows through the ridge gap, and
      the compression causes insertion of the payload into the cells; and
   moving the core from the processing position to a cleaning position relative to the shell when the pressure drop or the flow rate of cell media through the cell processing apparatus exceeds a threshold, wherein the ridge gap in the cleaning position is greater than in the processing position.

2. The method of claim 1, wherein flowing the cell media through the interior space comprises moving the core relative to the shell.

3. The method of claim 1, wherein moving the core relative to the shell comprises rotating the core relative to the shell.

4. The method of claim 1, wherein moving the core relative to the shell comprises linearly translating the core relative to the shell along a center axis of the cell processing apparatus.

5. The method of claim 1, wherein moving the core from the processing position to the cleaning position comprises linearly translating the core relative to the shell along a center axis of the cell processing apparatus.

6. The method of claim 5, wherein:
   the shell comprises a first shell portion and a second shell portion such that the inner shell cylindrical surface of the first shell portion is positioned closer to the center axis of the cell processing apparatus than the inner shell cylindrical surface of the second shell portion;
   in the processing position, the ridges are surrounded by the inner shell cylindrical surface of the first shell portion; and
   in the cleaning position, the ridges are surrounded by the inner shell cylindrical surface of the second shell portion.

7. The method of claim 1, wherein the ridges are supported on and protruding away from one of the inner shell cylindrical surface and the outer core cylindrical surface and toward another one of the inner shell cylindrical surface and the outer core cylindrical surface.

8. The method of claim 7, wherein the ridges are monolithic with one of the shell or the core.

9. The method of claim 1, wherein each of the ridges forms a continuous ring around the core.

10. The method of claim 1, wherein each of the ridges comprises petals separated from each other by petal gaps.

11. The method of claim 10, wherein the petals and the petal gaps of two adjacent ones of the ridges are angularly offset.

12. The method of claim 1, wherein the ridges are supported on and protruding away from the outer core cylindrical surface.

13. The method of claim 12, wherein an outer radius of each of the ridges is the same.

14. The method of claim 6, wherein:
   the second shell portion comprises a cleaning inlet and a cleaning outlet, and
   the method further comprises, while the core is in the cleaning position, flowing cleaning media through the second shell portion into the cleaning inlet, around the core, and out of the cleaning outlet.

15. The method of claim 14, wherein the first shell portion is fluidically isolated from the second shell portion while flowing the cleaning media through the second shell portion.

16. The method of claim 14, wherein the cleaning media removes uncompressible cells, aggregated around the ridges while flowing a cell media through the interior space of the cell processing apparatus.

17. The method of claim 1, wherein a radius of the inner shell cylindrical surface of the shell gradually increases along a center axis of the cell processing apparatus.

18. The method of claim 1, wherein at least one of the shell or the core is formed from metal.

19. The method of claim 1, wherein each of the inner shell cylindrical and the outer core cylindrical surface are circular.

20. The method of claim 1, wherein a portion of each of the ridges forming the ridge gap with one of the inner shell cylindrical surface and the outer core cylindrical surface is parallel to the one of the inner shell cylindrical surface and the outer core cylindrical surface.

* * * * *